(12) United States Patent
Zhang (10) Patent No.: US 7,276,246 B2
(45) Date of Patent: Oct. 2, 2007

(54) DISSOLVABLE BACKING LAYER FOR USE WITH A TRANSMUCOSAL DELIVERY DEVICE

(75) Inventor: Hao Zhang, Foster City, CA (US)

(73) Assignee: Cephalon, Inc., Frazer, PA (US)

( * ) Notice: Subject to any disclaimer, the term of this patent is extended or adjusted under 35 U.S.C. 154(b) by 687 days.

(21) Appl. No.: 10/841,892

(22) Filed: May 7, 2004

(65) Prior Publication Data

US 2004/0224007 A1 Nov. 11, 2004

Related U.S. Application Data (60) Provisional application No. 60/469,497, filed on May 9, 2003.

(51) Int. Cl.
*A61F 13/00* (2006.01)
*A61F 2/00* (2006.01)

(52) U.S. Cl. ...................... 424/434; 424/426

(58) Field of Classification Search ............ 424/426, 424/427, 428, 430, 434, 435, 436, 448, 449
See application file for complete search history.

(56) References Cited

U.S. PATENT DOCUMENTS

| | | | |
|---|---|---|---|
| 3,754,332 A * | 8/1973 | Warren, Jr. ............... | 433/217.1 |
| 4,226,848 A | 10/1980 | Nagai et al. | |
| 4,250,163 A | 2/1981 | Nagai et al. | |
| 4,292,299 A | 9/1981 | Suzuki et al. | |
| 4,307,075 A | 12/1981 | Martin | |
| 4,517,173 A | 5/1985 | Kizawa et al. | |
| 4,572,832 A | 2/1986 | Kigasawa et al. | |
| 4,573,996 A | 3/1986 | Kwiatek et al. | |
| 4,615,697 A | 10/1986 | Robinson | |
| 4,704,119 A | 11/1987 | Shaw et al. | |
| 4,713,243 A | 12/1987 | Schiraldi et al. | |
| 4,740,365 A | 4/1988 | Yukimatsu et al. | |
| 4,755,386 A | 7/1988 | Hsiao et al. | |
| 4,764,378 A | 8/1988 | Keith et al. | |
| 4,765,983 A | 8/1988 | Takayanagi et al. | |
| 4,788,209 A | 11/1988 | Baumann et al. | |
| 4,866,046 A | 9/1989 | Amer | |

(Continued)

FOREIGN PATENT DOCUMENTS

EP 0873750 10/1998

(Continued)

*Primary Examiner*—Sharon E. Kennedy (57) ABSTRACT

A water-dissolvable drug delivery device designed so as to reliably maintain a drug or active agent within a defined region against a mucosal surface. The drug delivery device comprises a water-dissolvable backing layer, an adhesive layer adjacent to at least a portion of the backing layer, and an active layer that is circumscribed by the backing layer and adhesive layer. The backing layer may optionally include a water-dissolvable hydrophilic region and a non-hydrophilic region at least partially encapsulated within the hydrophilic region that inhibits migration of water, drugs, or other active agents through the backing layer. The adhesive layer may be water-activated or it may have a peelable cover layer that, when removed, exposes the adhesive material. The active layer may comprise any drug or other active agent, either alone or in combination with (i) an enhancer that increases the ability of the drug or other active agent to diffuse through a mucosal membrane and/or (ii) a matrix material such as an alginate to hold the active layer together.

25 Claims, 3 Drawing Sheets

U.S. PATENT DOCUMENTS

| | | | |
|---|---|---|---|
| 4,876,092 A | 10/1989 | Mizobuchi et al. |
| 4,900,552 A | 2/1990 | Sanvordeker et al. |
| 4,900,554 A | 2/1990 | Yanagibashi et al. |
| 5,021,053 A | 6/1991 | Barclay et al. |
| 5,053,032 A | 10/1991 | Barclay et al. |
| 5,073,374 A | 12/1991 | McCarty |
| 5,110,605 A | 5/1992 | Acharya |
| 5,112,616 A | 5/1992 | McCarty |
| 5,113,860 A | 5/1992 | McQuinn |
| 5,147,648 A | 9/1992 | Bannert |
| 5,147,654 A | 9/1992 | Place et al. |
| 5,204,108 A | 4/1993 | Illum |
| 5,248,310 A | 9/1993 | Barclay et al. |
| 5,288,498 A | 2/1994 | Stanley et al. |
| 5,298,256 A | 3/1994 | Flockhart et al. |
| 5,326,685 A | 7/1994 | Gaglio et al. |
| 5,346,701 A | 9/1994 | Heiber et al. |
| 5,482,706 A | 1/1996 | Igari et al. |
| 5,512,293 A | 4/1996 | Landrau et al. |
| 5,512,299 A | 4/1996 | Place et al. |
| 5,516,523 A | 5/1996 | Heiber et al. |
| 5,529,782 A | 6/1996 | Staab |
| 5,573,776 A | 11/1996 | Harrison et al. |
| 5,578,315 A | 11/1996 | Chien et al. |
| 5,599,554 A | 2/1997 | Majeti et al. |
| 5,603,947 A | 2/1997 | Wong et al. |
| 5,624,677 A | 4/1997 | El-Rashidy et al. |
| 5,639,469 A | 6/1997 | Benes et al. |
| 5,650,192 A | 7/1997 | Britton et al. |
| 5,656,284 A | 8/1997 | Balkin |
| 5,679,373 A | 10/1997 | Wick et al. |
| 5,679,714 A | 10/1997 | Weg |
| 5,700,478 A | 12/1997 | Biegajski et al. |
| 5,725,853 A | 3/1998 | Dennis et al. |
| 5,750,136 A | 5/1998 | Scholz et al. |
| 5,763,476 A | 6/1998 | Delbressine et al. |
| 5,766,620 A | 6/1998 | Heiber et al. |
| 5,776,493 A | 7/1998 | Barclay et al. |
| 5,783,207 A | 7/1998 | Stanley et al. |
| 5,800,832 A | 9/1998 | Tapolsky et al. |
| 5,827,525 A | 10/1998 | Liao et al. |
| 5,849,322 A | 12/1998 | Ebert et al. |
| 5,855,908 A | 1/1999 | Stanley et al. |
| 5,863,555 A | 1/1999 | Heiber et al. |
| 5,869,096 A | 2/1999 | Barclay et al. |
| 5,888,534 A | 3/1999 | El-Rashidy et al. |
| 5,891,458 A | 4/1999 | Britton et al. |
| 5,900,247 A | 5/1999 | Rault et al. |
| 5,908,637 A | 6/1999 | Benes et al. |
| 5,981,552 A | 11/1999 | Alam |
| 5,989,582 A | 11/1999 | Weg |
| 6,087,362 A | 7/2000 | El-Rashidy |
| 6,117,446 A | 9/2000 | Place |
| 6,121,276 A | 9/2000 | El-Rashidy et al. |
| 6,146,655 A | 11/2000 | Ruben |
| 6,147,102 A | 11/2000 | Borgman |
| 6,159,498 A | 12/2000 | Tapolsky et al. |
| 6,177,096 B1 | 1/2001 | Zerbe et al. |
| 6,180,682 B1 | 1/2001 | Place |
| 6,183,775 B1 | 2/2001 | Ventouras |
| 6,193,992 B1 | 2/2001 | El-Rashidy et al. |
| 6,197,331 B1 | 3/2001 | Lerner et al. |
| 6,200,593 B1 | 3/2001 | Place |
| 6,200,604 B1 | 3/2001 | Pather et al. |
| 6,210,699 B1 | 4/2001 | Acharya et al. |
| 6,221,379 B1 | 4/2001 | Place |
| 6,228,864 B1 | 5/2001 | Smith et al. |
| 6,241,529 B1 | 6/2001 | Place |
| 6,242,004 B1 | 6/2001 | Rault |
| 6,248,789 B1 | 6/2001 | Weg |
| 6,255,502 B1 | 7/2001 | Penkler et al. |
| 6,264,974 B1 | 7/2001 | Madhat |
| 6,264,981 B1 | 7/2001 | Zhang et al. |
| 6,284,262 B1 | 9/2001 | Place |
| 6,284,263 B1 | 9/2001 | Place |
| 6,284,264 B1 | 9/2001 | Zerbe et al. |
| 6,294,550 B1 | 9/2001 | Place et al. |
| 6,306,437 B1 | 10/2001 | El-Rashidy et al. |
| 6,306,841 B1 | 10/2001 | Place et al. |
| 6,319,510 B1 | 11/2001 | Yates |
| 6,375,963 B1 | 4/2002 | Repka et al. |
| 6,585,997 B2 * | 7/2003 | Moro et al. .................. 424/434 |
| 2001/0006677 A1 | 7/2001 | McGinity et al. |
| 2002/0068151 A1 | 6/2002 | Kim et al. |
| 2004/0028732 A1 | 2/2004 | Falkenhausen et al. |

FOREIGN PATENT DOCUMENTS

| | | |
|---|---|---|
| WO | WO99/55312 | 11/1999 |
| WO | WO 00/72827 | 12/2000 |
| WO | WO 02/02085 | 1/2002 |
| WO | WO 03/015748 | 2/2003 |

* cited by examiner

Interferon serum concentration after buccal patch application containing 1 mg interferon and 8 mg sodium taurocholate

FIG. 9

Serum sumatriptan concentration after application of buccal sumatriptan patch containing 8.82 mg sumatriptan and 4.70 mg sodium taurocholate

FIG. 10

DISSOLVABLE BACKING LAYER FOR USE WITH A TRANSMUCOSAL DELIVERY DEVICE

This Application claims benefit of U.S. provisional Application Ser. No. 60/469,497 filed May 9, 2003.

BACKGROUND OF THE INVENTION

The present invention is in the field of transmucosal delivery devices used to deliver drugs or other active agents across mucosal tissues. More particularly, the present invention involves dissolvable transmucosal delivery devices that can be used to isolate a drug or other active agent against a mucosal layer but which will dissolve or otherwise disintegrate over time when exposed to moisture (e.g., saliva).

The Relevant Technology

Oral mucosal drug delivery is an alternative method of systemic drug delivery. It offers several advantages over both injectable and enteral delivery. Drugs absorbed via the oral mucosa avoid the low pH gastric fluid and proteases, as well as first-pass metabolism in the liver. The onset of action is faster than oral administration. Unlike injections, oral transmucosal delivery is non-invasive and not painful. Moreover, a patient can administrer the medicine without help from a medical professional.

There is considerable interest in developing new dosage forms that can deliver drugs and other active agents across the oral mucosa of humans and other living things. In general, oral transmucosal dosage forms can be classified in one of three categories: (1) solid forms, (2) gum, and (3) patches. Examples of common solid dosage forms include lozenges, lozenges on a stick (e.g., lollipops), buccal tablets, and sublingual tablets. As the solid matrix dissolves or otherwise disintegrates in the oral cavity it releases the drug, which is absorbed by the oral mucosa. This type of dosage form is referred to as an "open system" because saliva can flow freely to and from the dosage form to dissolve or otherwise disintegrate the formulation. Drug concentration is generally controlled by how fast the matrix dissolves or otherwise disintegrates, which is controlled by how fast the patient sucks the unit.

Gum, like lozenges and tablets, is an open system. When this dosage form is chewed the drug is released from gum into the oral cavity where it can be absorbed by oral mucosa. Drug release from gum is controlled by the make up of the delivery device, as well as how fast the gum is chewed. In general, gum dosage forms last longer than lozenges or tablets.

The term "buccal patch" typically refers to a flexible film that adheres to the oral mucosa and delivers a drug over a period of time. The buccal patch dosage form can be further divided into three types or subcategories: (1) dissolvable matrix patches, (2) patches having a non-dissolvable backing, and (3) patches with a dissolvable backing. For examples known in the art of buccal patch technology see U.S. Pat. No. 3,598,122; U.S. Pat. No. 3,972,995; U.S. Pat. No. 4,517,173; U.S. Pat. No. 4,573,996; U.S. Pat. No. 4,572,832; U.S. Pat. No. 4,704,119; U.S. Pat. No. 4,713,243; U.S. Pat. No. 4,715,369; U.S. Pat. No. 4,740,365; U.S. Pat. No. 4,855,142; U.S. Pat. No. 4,876,092; U.S. Pat. No. 4,900,552; U.S. Pat. No. 4,900,554; U.S. Pat. No. 5,137,729; U.S. Pat. No. 5,298,256; U.S. Pat. No. 5,346,701; U.S. Pat. No. 5,516,523; U.S. Pat. No. 5,578,315; U.S. Pat. No. 5,599,554; U.S. Pat. No. 5,639,469; U.S. Pat. No. 5,766,620; U.S. Pat. No. 5,800,832; U.S. Pat. No. 5,863,555; U.S. Pat. No. 5,900,247; U.S. Pat. No. 6,159,498; U.S. Pat. No. 6,210,699; and U.S. Pat. No. 6,319,510.

Dissolvable matrix patches work similar to gum, lozenge and tablet dosage forms. The dissolving matrix releases the drug into the oral cavity for absorption by oral mucosa. They usually last longer than lozenges or tablets. Unlike gum, dissolvable matrix patches release the drug passively rather than actively. One limitation of all these systems is that the drug concentration is not well controlled.

In order to control the drug concentration over the period of drug delivery, buccal patches with backings were developed. Controlling drug concentration is particularly important when mucosally delivering drugs that require the help of permeation enhancers. Permeation enhancers are chemicals that can temporarily compromise the integrity of the oral mucosa so that drug delivery can be enhanced. The concentration of enhancers needs to be carefully controlled. If the concentration is too high, the enhancer can cause mucosal irritation or damage. If too low, it may not provide the desired enhancement of drug delivery. One way to maintain control of both drug and enhancer concentration is to include a backing so that the active formulation of the buccal patch is completely isolated from the surrounding environment.

There are two types of backing systems in the buccal patch dosage form: dissolvable and non-dissolvable. Non-dissolvable backings are usually flexible. They are designed to stay in the oral cavity for long periods of time, e.g., up to 10-15 hours. The disadvantage is that the patch has to be removed from oral mucosa by the patient after drug administration.

Patches with dissolvable backings are designed to stay in the oral cavity for a short period of time. It is intended for the backing to control the local environment inside the patch so that high efficient drug delivery can be achieved in a controlled fashion. Over time, it is intended for the backing to dissolve or disintegrate in the oral cavity (e.g., when exposed to saliva) in order for all or part of the delivery device to go away. This eliminates the need to remove the patch after treatment is complete.

One of the challenges of providing patches with a dissolvable or disintegratable backing has been the need to provide materials that are able to provide an adequate barrier while still being able to dissolve or disintegrate over time. Another challenge inherent in transmucosal delivery of drugs or other active agents, particularly within the oral cavity, is the need to isolate and maintain the drug or other active agent against the mucosal layer. Otherwise, the active agent may diffuse into the oral cavity where it can inadvertently or deliberately be swallowed or expectorated from the mouth. In either case, the drug or other active agent will not be able to pass through the mucosal membrane as intended. The challenge, therefore, is to provide a transmucosal delivery device that is able to both isolate and maintain a drug or other active agent against the mucosal surface while also being able to dissolve over time in the presence of moisture.

SUMMARY OF THE INVENTION

The present invention comprises water-dissolvable or disintegratable delivery devices used to transmucosally deliver drugs or other active agents across an oral mucosal membrane. Such devices are able to isolate and maintain a drug or other active agent against the mucosal surface during a prescribed period of time but which will dissolve or otherwise disintegrate when exposed to moisture (e.g., when exposed to saliva within the oral cavity of a patient).

The transmucosal delivery devices according to the invention include at least three separate and identifiable layers that act together to isolate and maintain the drug or other active agent against the mucosal surface during a prescribed period of time in order for the drug or other active agent to diffuse through the mucosal membrane. At some point during or after such diffusion of the drug or other active agent, the delivery device is able to dissolve or otherwise disintegrate so as to obviate the need to physically remove it from the mucosal surface after completion of the desired treatment.

The three primary layers or regions within delivery devices according to the invention include (1) a dissolvable backing layer, (2) an adhesive layer adjacent to at least a portion of the backing layer, and (3) an active layer adjacent to at least one of the backing or adhesive layers. The backing layer is sized and configured so as to extend beyond the outer perimeter of the active layer. In this way, the backing layer circumscribes the active layer. The adhesive layer similarly circumscribes the active layer in order to reliably adhere the backing layer to the mucosal surface when in use in order to effectively isolate the active layer within a confined circumscribed region against the mucosal surface. In this way, the backing layer and adhesive layer work together to maintain the drug or other active agent within the active layer within a confined region against the surface of the mucosal membrane through which it is intended for it to diffuse.

In a preferred embodiment, the backing layer is sized and formulated so as to remain intact during a prescribed time period required for the drug or other active agent within the active layer to diffuse through the mucosal membrane. In this way, the backing layer is able to provide a physical and/or chemical barrier between the active layer and the surrounding fluids that might otherwise draw the drug or other active agent away from the mucosal membrane surface (e.g., into the saliva of the oral cavity). In order for the backing layer to be dissolvable or disintegratable when exposed to moisture over time, the backing layer will generally comprise one or more hydrophilic polymers that are sensitive to moisture.

Because the ability of the backing layer to prevent diffusion of the drug or other active agent away from the mucosal surface is only as good as its ability to provide a barrier, both behind the active layer and around its perimeter, the adhesive layer synergistically works in conjunction with the backing layer to provide a barrier that extends over and circumscribes the active layer when in use. For example, a dissolvable backing layer that is able to pull away from the mucosal surface, however little, may provide a path through which mucosal fluids can enter and have access to the active layer and through which the drug or other active agent can be expressed, leached or diffuse, thereby undermining the ability of the backing layer to isolate and maintain the active agents against the mucosal surface as intended. The adhesive layer prevents undesired detachment of the backing layer from the mucosal surface.

It will be preferable for the backing layer to be slippery when exposed to moisture and for the adhesive region circumscribing the active layer to remain. Otherwise, the delivery device could be inadvertently removed from the mucosal surface, such as by pressing a tongue or other opposing mucosal surface against the backing layer and then withdrawing it from the mucosal surface.

In order to increase the barrier properties of the delivery device during use, it is within the scope of the invention to optionally utilize a backing layer comprising separate hydrophilic and non-hydrophilic regions. The hydrophilic and non-hydrophilic regions work together to provide good dissolvability or disintegratability in moisture of a prescribed period of time while further inhibiting the diffusion of water, drugs, or other active agent therethrough compared to backing layers that do not contain a non-hydrophilic region.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE INVENTION

The present invention relates to water-dissolvable or disintegratable delivery devices used to transmucosally deliver drugs or other active agents across the oral mucosa of human or other living animals. The inventive transmucosal delivery devices are suitable for isolating and maintaining a drug or other active agent against the mucosal surface during a prescribed period of time but which will dissolve or otherwise disintegrate when exposed to moisture (e.g., when exposed to saliva within the oral cavity of a patient).

The transmucosal delivery devices comprise three primary layers that act together to isolate and maintain the drug or active agent against a mucosal surface. They include: (1) a dissolvable backing layer; (2) an adhesive layer adjacent to and circumscribed by at least a portion of the backing layer; and (3) an active layer adjacent to at least one of the backing or adhesive layers.

Compositions

The inventive transmucosal delivery devices according to the invention may include a variety of different components which can be blended together or attached as layers in order to yield a delivery device comprising the three primary layers described above.

As used in the specification and claims, the terms "dissolve" and "dissolvable" include, but are not necessarily limited to, what is meant by the terms "dissolve" or "disintegrate" and "dissolvable" or "disintegratable", respectively. Similarly, the term "water-dissolvable" includes, but is not limited to, what is meant by the term "water-disintegratable". For example, as used herein a dissolvable layer may separate into components when exposed to moisture and optionally passing into solution or it may pass directly into solution when exposed to moisture.

Dissolvable Backing Layer

The dissolvable backing layer generally comprises one or more hydrophilic polymers that have the property of being dissolvable in saliva or moisture of an oral cavity. Examples of hydrophilic polymers that may be used in accordance with the invention include, but are not limited to, gelatin, caseine, other protein-based materials, pectin, agarose (agar), chitosan, carrageenan, starch, dextran, methylcellulose, calcium carboxymethylcellulose, sodium carboxymethyl cellulose, cross-linked polymer of sodium carboxymethylcellulose (e.g., croscarmellose sodium), microcrystalline cellulose, ethylcellulose, hydroxyethylcellulose, hydroxypropylcellulose, hydroxypropylmethylcellulose, hydroxypropylmethylcellulose phthalate, cellulose ethers, cellulose acetate, cellulose acetate phthalate, other cellulose derivatives, polyvinyl alcohol, polyvinylpyrrolidone (PVP), cross-linked povidone, other vinyl polymers and copolymers, guar gum, poloxamer, polyethylene glycol, polyethylene oxide, polyacrylic acid, polyethers, alkoxy polymers, sodium alginate, xanthan gum, other natural hydrogels, and hydrogels derived from natural products. Preferred examples of hydrophilic polymers that may be used in accordance with the invention include, but are not limited to, gelatin and sodium alginate.

In addition to the hydrophilic polymer, solvents or plasticizers may be used, which make the backing layer more flexible. Examples of plasticizers include, but are not limited to, glycerin, propylene glycol, polyethylene glycol, polypropylene glycol, sugar alcohols, and corn syrup. The hydrophilic region may also include a surfactant or emulsifier so that a non-hydrophilic region, if present, is more stable in the hydrophilic region. The backing layer may also include other components, such as flavorants, sweeteners, coloring agents, antiseptic agents, preservatives, non-hydrophilic materials, and other ingredients so that the delivery device is more stable and promotes better patient compliance.

In order to increase the barrier properties of the delivery device during use, it is within the scope of the invention to optionally utilize a backing layer comprising distinct hydrophilic and non-hydrophilic regions. The term "non-hydrophilic region" shall refer to any region or regions other than the hydrophilic region. The hydrophilic and non-hydrophilic regions work together to provide good dissolvability in moisture of a prescribed period of time while further inhibiting the diffusion of water, a drug, or other active agent therethrough compared to baking layers that do not contain at least one non-hydrophilic region.

In one embodiment, the hydrophilic region will comprise a continuous phase that substantially or entirely surrounds or encompasses the non-hydrophilic region. Nevertheless, it is certainly within the scope of the invention to provide a non-hydrophilic region comprising two or more distinct subregions, layers or components.

The time in which the hydrophilic region or component will dissolve when exposed to moisture (e.g., saliva) depends on a number of factors. These include the identity and concentrations of the various components within the hydrophilic region, the components within the non-hydrophilic region discussed more fully below, as well as their size, the thickness of the overall backing layer, the amount of moisture to which the backing layer is exposed, and the existence of agitation, movement or other external forces (e.g., tongue movements) that might accelerate the breakdown or dissolution of the backing layer.

In general, the concentration of the hydrophilic polymer within the hydrophilic region will be in a range of about 1% to 100% by weight of the hydrophilic region, more preferably in a range from about 5% to about 90%, and most preferably in a range from about 10% to about 80% by weight of the hydrophilic region.

The concentration of the solvent or plasticizer within the hydrophilic region will be in a range from 0% to about 80% by weight of the hydrophilic region, more preferably in a range from about 2% to about 60%, and most preferably in a range from about 5% to about 50% by weight of the hydrophilic region.

The hydrophilic region will preferably comprise from about 10% to about 95% percent by volume of the overall backing layer, more preferably from about 15% to about 90%, and most preferably from about 20% to about 85% by volume of the backing layer.

The non-hydrophilic region may comprise either a disperse phase or a continuous phase relative to the hydrophilic region. The main purpose of the non-hydrophilic region is to inhibit or slow migration of water, drugs or other active agents or molecules through the backing layer compared to a backing layer in the absence of the non-hydrophilic region. The level of inhibition or slowing of migration need not be dramatic, but appreciably measurable. Nevertheless, in more preferred embodiments according to the invention, the inhibition or slowing of migration will be substantial (e.g., so that it takes many times longer for the targeted molecule to diffuse through the backing layer compared to a backing layer in the absence of the non-hydrophilic region).

Examples of non-hydrophilic materials that can be used to form one or more non-hydrophilic regions within the hydrophilic region include a disperse phase of gaseous voids (e.g., air bubbles), a continuous or disperse phase of hydrophobic liquids, a continuous or disperse phase of solid or semi-solid hydrophobic materials, and a continuous or disperse phase of solid particles that are not necessarily chemically hydrophobic but that are not readily water soluble (e.g., solid non water-dissolvable particles and solid hydrophobic particles).

Examples of hydrophobic liquids that may be dispersed in droplet form throughout the hydrophilic region so as to form a disperse non-hydrophilic region include, but are not limited to, oil, vegetable oils, mineral oil, silicones, and organic polymers.

Examples of solid or semi-solid non-hydrophilic materials that may be dispersed throughout the hydrophilic region so as to form a disperse non-hydrophilic region include, but are not limited to, a wide variety of hydrogenated vegetable oil, waxes, magnesium stearate, fats, fatty acids, salts of fatty acids, polymers, polymeric beads, and silicone particles.

Examples of solid particles that are not necessarily chemically hydrophobic but that are not readily water soluble and that may be dispersed throughout the hydrophilic region so as to form a disperse non-hydrophilic region include water-insoluble inorganic filler particles, examples of which include, but are not limited to, talc, sand, silica, alumina, transition metal oxides (e.g., titanium dioxide), silicates, ground geologic materials, and limestone.

As can be readily seen, virtually any material, whether in a gaseous, liquid or solid phase, can comprise the non-hydrophilic region, the only limitation being that such material provides a substantially higher barrier to water, drugs, or other active agents than the hydrophilic region. In general, it is contemplated that any GRAS ("generally regarded as safe") material can be used safely within the oral cavity in the case of a backing layer intended for use in a buccal patch or other transmucosal delivery device.

Instead of a disperse phase, the non-hydrophilic region may comprise a continuous phase that effectively forms a continuous shield or barrier so as to prevent, inhibit or slow migration of the water, drugs, active agents, or other molecules through the backing layer. In one embodiment, the continuous non-hydrophilic region may comprise a continuous phase that is entirely encapsulated within the hydrophilic region, or which bifurcates the hydrophilic region into two or more subregions or layers. The non-hydrophilic region may comprise a plurality of subregions that are sufficiently large so as to effectively constitute a plurality of continuous phases rather than a disperse phase, although the notion of what constitutes a disperse phase rather than a plurality of continuous phases is a sliding scale. The continuous non-hydrophilic region or component may comprise a thin layer of a liquid or solid non-hydrophilic material that is interposed between an active layer or region containing a drug or other target molecule and at least a portion of the hydrophilic region.

In the case where the non-hydrophilic region comprises a disperse phase of relatively small gaseous voids, hydrophobic liquid droplets or particles, the non-hydrophilic material may generally comprise any desired non-hydrophilic material. This is because, as the hydrophilic region dissolves over time when exposed to moisture, the hydrophobic liquid droplets or particles dispersed with the hydrophilic region will also readily disperse within the oral cavity or other place of attachment of the delivery device.

On the other hand, in the case where the non-hydrophilic region comprises one or more continuous regions of substantial size, it may be preferable for the material used to form the non-hydrophilic region to comprise a material that is substantially liquid or otherwise easily broken up and dispersed, at least at body temperature. Where the material comprising the non-hydrophilic region is a liquid at room temperature, it will generally readily disperse upon disintegration of the hydrophilic region. It is also within the scope of the invention to select a material that may be a solid or semi-solid at room temperature but which softens sufficiently when raised to body temperature so as to become more easily dispersible upon disintegration of the hydrophilic region.

The non-hydrophilic region will preferably comprise from about 5% to about 90% by volume of the overall backing layer, more preferably from about 10% to about 85%, and most preferably from about 15% to about 80% by volume of the backing layer.

The thickness of the backing layer generally correlates with the time it takes for the backing layer to become substantially dissolved when exposed to moisture (e.g., saliva). In general, the backing layer, as a finished product after drying, will preferably have a thickness in a range from about 0.1 mm to about 5 mm, more preferably in a range from about 0.2 mm to about 3.5 mm, and most preferably in a range from about 0.3 mm to about 2 mm.

The backing layer can be formulated and sized so as to yield a backing layer that becomes dissolved within the oral cavity when exposed to saliva within a prescribed time period or range (or when exposed to moisture in some other region of the body). For example, the backing layer according to the invention may have a formulation and thickness in order for the backing layer to become dissolved within the oral cavity when exposed to saliva within a time period and a range from about 1 minute to about 2 hours, more preferably in a range from about 10 minutes to about 1 hour.

Furthermore, it is only necessary for the non-hydrophilic region to inhibit or slow migration of water, drugs, other active agents, or other molecules through the backing layer by some measurable amount compared to a backing layer in the absence of the non-hydrophilic region. In general, backing layers according to the invention will preferably decrease the permeability coefficient of water, drug, other active agents, or at least one other molecule by at least about 25%, more preferably by at least about 50%, and most preferably by at least about 75% compared to a backing layer in the absence of the non-hydrophilic region.

Adhesive Layer

The adhesive layer may comprise any type of adhesive material that is able to adhere to a mucosal surface. The term "adhesive" as used herein refers to the phenomenon where a natural or synthetic substance applied to a wet mucosal epithelium adheres, usually creating a new interface, to the mucous layer. (CRC Critical Review in Ther. Drug Carrier, Vol. 5, Issue 1, p. 21 (1988)). Generally mucoadhesion can be achieved via physical or chemical processes or both. This mechanism is described in Journal of Controlled Release, Vol. 2, p257 (1982) and Journal of Controlled Release Vol. 18 (1992) p. 249. The above references are incorporated by reference herein in their entirety. The adhesive layer may be substantially non-adhesive or less adhesive when dry but that becomes substantially adhesive when moistened, e.g., by being placed against a moist mucosal surface. In some cases, the adhesive properties may increase up to a certain level of moistening, after which the adhesive properties may drop if over-moistened. In such cases, the backing layer will help to protect over-moistening of the adhesive layer while still intact and prior to dissolving. After a period of time, however, the water-dissolvable backing layer will dissolve, at which time the adhesive layer will be exposed to increased moisture.

In the alternative, the adhesive layer may comprise an adhesive material that is adhesive without moistening. In such cases it may be advantageous to include a removable cover that can be peeled off at the time of use to expose a surface of the adhesive layer to be placed against the mucosal surface.

Examples of suitable adhesive materials, or mucoadhesive polymers as used herein, include, but are not limited to, polyacrylic acid polymers (e.g., Carbopol® (B.F. Goodrich Co.) and Pemulen® (B.F. Goodrich Co.)), polyethylene oxides (e.g., polyethylene glycol), starches, cellulose ethers and their salts, carrageenan, sodium alginate, and mixtures of the foregoing with one or more of the hydrophilic polymers listed above with respect to the backing layer. Preferred examples of suitable adhesive materials include, but are not limited to, Polyox® 750 (a polyethylene oxide, water soluble resin) and Carbopol® 971.

In addition to mucoadhesive polymers, the adhesive layer may also include plasticizers, sweeteners, flavor agents, preservatives, or other additives so that the adhesive layer is flexible and/or to promote patient compliance.

The adhesive layer may be attached to part or all of a surface of the backing layer, as discussed more fully below with respect to the drawings. The adhesive layer will generally extend beyond the active layer in order to reliably adhere to the mucosa and form a barrier around the active layer so as to isolate and maintain the drug or other active agent contained within the active layer against a targeted area of the mucosal surface.

The thickness of the adhesive layer may be adjusted in order to provide a desired level of adhesion while also being able to dissolve when exposed to moisture over time, particularly upon dissolution of the backing layer. In general, the adhesive layer, as a finished product after drying, will preferably have a thickness and range from about 10 microns to about 1 mm, more preferably in a range from about 20 microns to about 0.5 mm, and most preferably in a range from about 30 microns to about 200 microns.

Active Layer

The active layer generally comprises one or more drugs or other active agents, a matrix material that holds the active layer together, and optionally an enhancer. In general, the active layer may comprise any known or future developed drug or other active agent known in the art. The enhancer may be used to accelerate diffusion of the drug or other active agent across the mucosal membrane.

Examples of drugs that may be included within the active layer according to the invention include, but are not limited to, fentanyl, codeine, sufentanil, lofentanil, carfentanil, alfentunil, morphine, other opiates, sumatriptan, other triptans, interferons, heparin, proteins, peptides, barbiturates, analgesics, anesthetics, anxolytics, sedatives, anti-depressants, cannobinoids, anticoagulants, anti-biotics, antihistamines, blood pressure modulators, and anti-cholesterol drugs, etc. Preferred examples include, but are not limited to, fentanyl, sufentanil, lofentanil, carfentanil, alfentunil, sumatriptan, other triptans, interferons, proteins, and peptides. More preferred examples include, but are not limited to, sumatriptan, other triptans, interferons, proteins, peptides, or any drug that requires an enhancer.

Examples of enhancers that may be used to facilitate or accelerate delivery of a drug or other active agent through the mucosal membrane, particularly hydrophilic molecules that may otherwise be difficult to diffuse through the mucosal membrane, include, but are not limited to, bile acid, their salt forms and derivatives, acyl carnitines, sodium dodecylsulfate, dimethylsulfoxide, sodium laurylsulfate, salts and other derivatives of saturated and unsaturated fatty acids, surfactants, alcohols, terpenes, cyclodextrins and their derivatives, saponins and their derivatives, chitosan, and chelators (e.g., EDTA, citric acid and salicylates). Examples of bile acids, their salt forms and derivatives, include, but are not limited to, cholic acid, dehydrocholic acid, glycocholic acid, glycodeoxycholic acid, deoxycholic acid, lithocholic acid, chenocholic acid, chenodeoxycholic acid, glycochenocholic acid, taurocholic acid, taurodeoxycholic acid, taurochenocholic acid, taurochenodeoxycholic acid, ursocholic acid, ursodeoxycholic acid, and hyodeoxycholic acid, and the like.

Examples of suitable matrix materials that may optionally be included in addition to the drug and enhancer include, but are not limited to, alginic acid, its salts and derivatives, celluloses, cellulose ethers, their salts and derivatives, starches, carrageenan, polyethylene glycol, polyethylene oxide, polyvinyl alcohol, polyvinyl pyrrolidone, acacia, and polyacrylic acids.

The thickness of the active layer generally correlates with the quantity of the drug or active agent contained therein, together with any optional ingredients such as the enhancer and/or matrix material. To provide a given quantity of drug or other active agent, the thickness of the active layer will be generally inversely proportional to the length or width dimensions. In general, the active layer, as a finished product after drying, will preferably have a thickness in a range from about 0.1 mm to about 2 mm, more preferably in a range from about 0.2 mm to about 1.5 mm, and most preferably in a range from about 0.3 mm to about 1.0 mm.

The dissolvable backing layer, the adhesive layer and/or the active layer, as disclosed herein, may optionally contain flavorants and/or sweeteners. In addition to flavorants known to one skilled in the art, examples of flavorants include, but are not limited to, mint (for example, peppermint or spearmintl), citrus oils (for example, lemon, lime, orange, or grapefruit), fruit essences (for example, berry, cherry, or grape), coconut, chocolate, clove, wintergreen, anise, vanilla, or combinations thereof. In addition to sweeteners known to one skilled in the art, examples of sweeteners include, but are not limited to, water-soluble sweeteners such as monosaccharides, disaccharides, and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof; as well as water-soluble artificial sweeteners such as the saccharin salts, cyclamate salts, stevia, aspartame, and acesulfame potassium.

Exemplary Drug Delivery Devices

Figure 1:
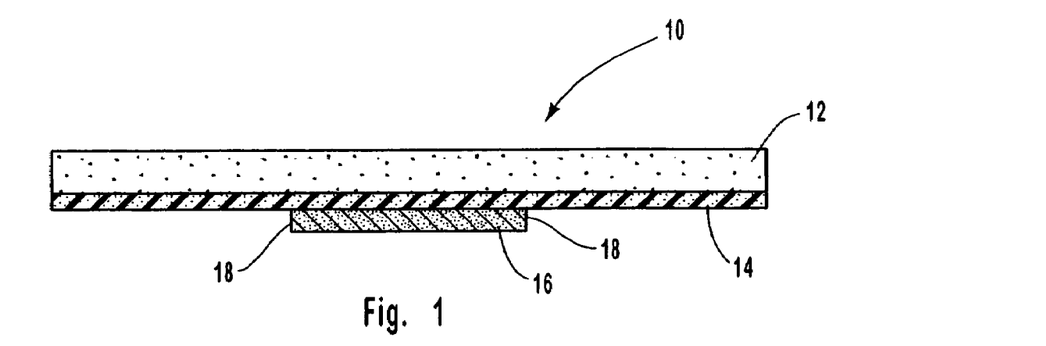
FIG. 1 is a cross-section view illustrating a transmucosal delivery device according to the invention that includes a dissolvable backing layer, an adhesive layer adjacent to the backing layer, and an active layer adjacent to and circumscribed by the adhesive layer.

Reference is now made to the drawings, which illustrate a number of exemplary transmucosal delivery devices within the scope of the invention. FIG. 1 depicts a transmucosal delivery device comprising a water-dissolvable backing layer 12, an adhesive layer 14 and an active layer 16. In this embodiment, the adhesive layer 14 extends along an entire length of the backing layer 12 and forms a separate and distinct layer that separates the backing layer 12 from the active layer 16. Both the backing layer 12 and the adhesive layer 14 extend beyond an outer perimeter 18 of the active layer 16 in order to circumscribe the active layer 16. In this way, the backing layer 12 and adhesive layer 14 work together to form a barrier behind and around the active layer 16 when the delivery device 10 is attached to a mucosal surface (not shown).

In one embodiment, the backing layer 12 and adhesive layer 14 may be formulated in order for the backing layer 12 and adhesive layer 14 to form an effective barrier for a prescribed time period during which the drug or other active agent within the active layer 16 will be isolated and maintained within a confined area or region against the mucosal surface (not shown). This prevents the drug or other agent from undesirably diffusing away from the confined area or region into, e.g., the oral cavity, where they may be swallowed and/or expectorated, inadvertently or otherwise. This may be particularly useful in the case where the delivery device is a buccal patch.

Figure 2:
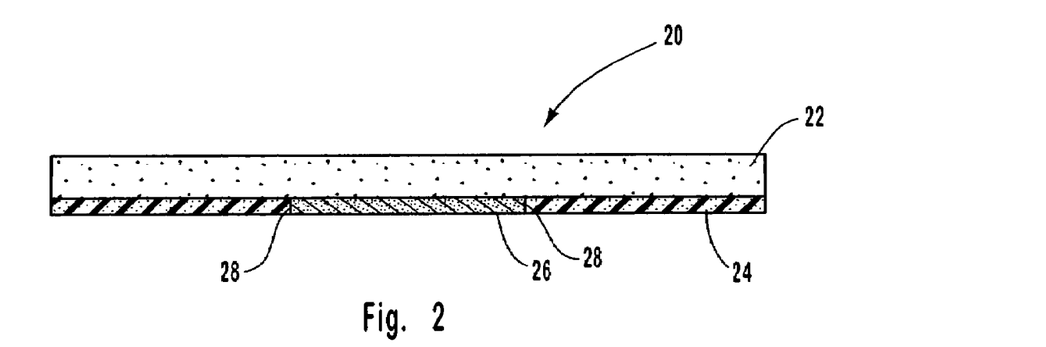
FIG. 2 is a cross-section view illustrating an alternative transmucosal delivery device comprising a dissolvable backing layer, an adhesive layer adjacent to a portion of the backing layer and an active layer adjacent to the backing layer and circumscribed by the adhesive layer.

FIG. 2 illustrates an alternative transmucosal delivery device 20 according to the invention that includes a water-dissolvable backing layer 22, an adhesive layer 24 adjacent to a portion of the backing layer 22, and an active layer 26 adjacent to the backing layer 22. In this embodiment, the adhesive layer 26 occupies a space or discontinuity where there is no adhesive layer 24 next to the backing layer 22. The backing layer 22 and the adhesive layer 24 extend beyond and circumscribe an outer perimeter 28 of the active layer 26 in order to provide a seal around the perimeter of the active layer 26. In this embodiment, the adhesive layer 24 and active layer 26 are substantially flush such that that they together form a continuous bottom surface.

Figure 3:
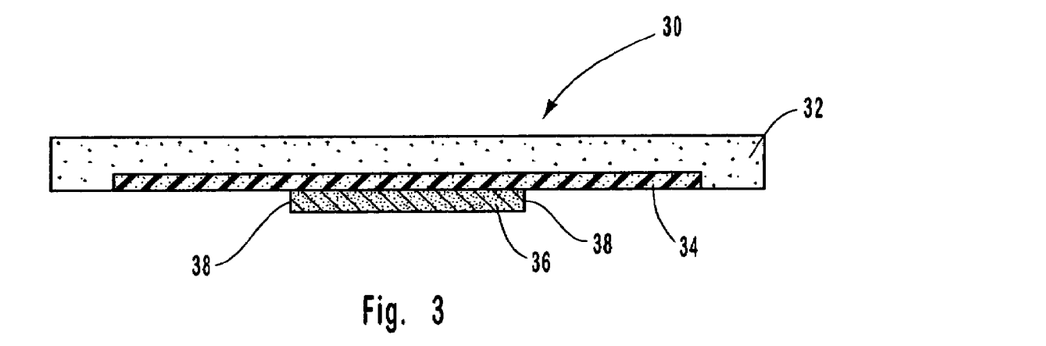
FIG. 3 is a cross-section view illustrating an alternative embodiment of a transmucosal delivery device comprising a dissolvable backing layer, an adhesive layer adjacent to and circumscribed by the backing layer, and an active layer adjacent to and circumscribed by the adhesive layer.

FIG. 3 illustrates an alternative transmucosal delivery device 30 according to the invention comprising a water-dissolvable backing layer 32, an adhesive layer 34 adjacent to the backing layer 32, and an active layer 36 adjacent to adhesive layer 34. In this embodiment, the backing layer 32 extends beyond and circumscribes the adhesive layer 34. Both the backing layer 32 and the adhesive layer 34 extend beyond and circumscribe an outer perimeter 38 of the active layer. As above, the adhesive layer 34 forms an effective seal around the perimeter 38 of the active layer 36 when the delivery device 30 is attached to a mucosal surface (not shown).

Figure 4:
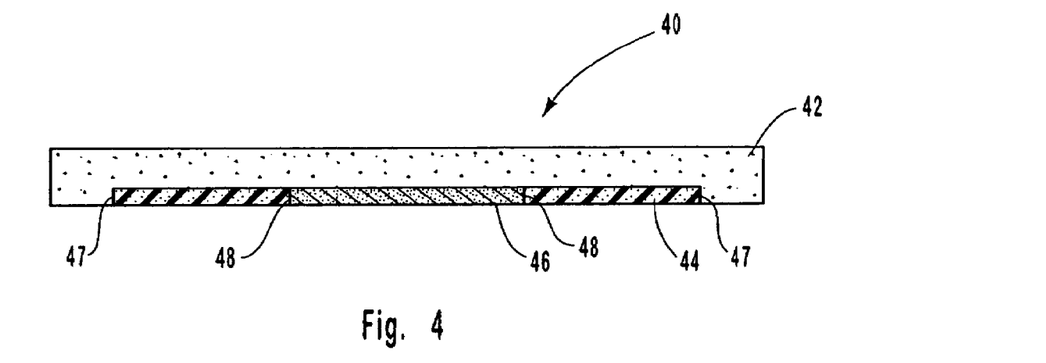
FIG. 4 is a cross-section view illustrating an alternative transmucosal delivery device comprising a dissolvable backing layer, an adhesive layer adjacent to and circumscribed by the backing layer, and an active layer adjacent to a portion of the backing layer and circumscribed the by the adhesive layer.

FIG. 4 depicts an alternative delivery device 40 according to the invention comprising a water-dissolvable backing layer 42, an adhesive layer or region 44 adjacent to a portion of the backing layer 42, and an active layer 46 adjacent to the backing layer 42. A portion of the backing layer 42 extends beyond and circumscribes an outer perimeter 47 of the adhesive layer. Both the backing layer 42 and adhesive layer 46 extend beyond and circumscribe a perimeter 48 of the active layer 46. As above, the adhesive layer 44 forms an effective seal around the perimeter 48 of the active layer 46 when the delivery device 40 is attached to a mucosal surface (not shown).

Figure 5:
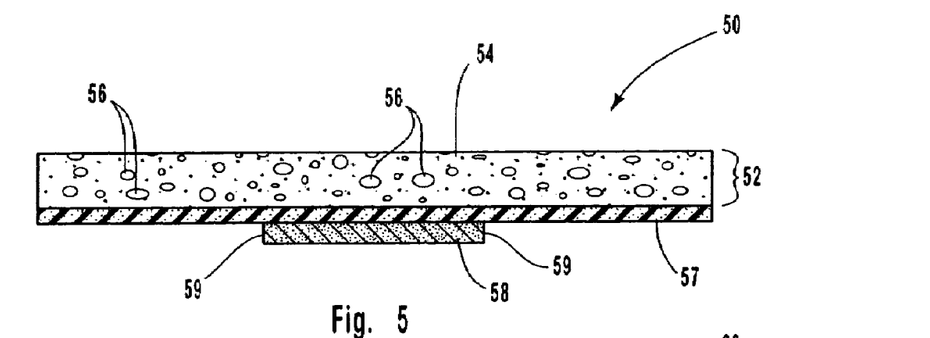
FIG. 5 is a cross-section view illustrating a transmucosal delivery device according to the invention that is similar to the device depicted in FIG. 1, but which includes a backing layer having distinct hydrophilic and non-hydrophilic regions that are configured so as to inhibit diffusion of targeted molecules from the active layer through the backing layer.

FIG. 5 depicts an alternative embodiment of a transmucosal delivery device 50 according to the invention comprising a water-dissolvable backing layer 52 that includes a hydrophilic region 54 and a non-hydrophilic region 56. The non-hydrophilic region refers to any region or regions other than the hydrophilic region. The non-hydrophilic region 56 of FIG. 5 is an example of a disperse phase.

An adhesive layer 57 is disposed adjacent to an entire length of the backing layer 52. An active layer 58 is disposed adjacent to a portion of the adhesive layer 57. The backing layer 52 and adhesive layer 57 extend beyond and circumscribe an outer perimeter 59 of the active layer 58. The adhesive layer 57 forms an effective seal around the perimeter 59 of the active layer 58 when the delivery device 50 is attached to a mucosal surface (not shown).

The purpose of the disperse non-hydrophilic region 56 is to inhibit migration of water, drugs, or other active agents contained within the active layer through the backing layer 52 during use of the delivery device 50 to deliver a drug or other active agent through a mucosal surface (not shown). It has been found that including a dispersed non-hydrophilic region 56 inhibits migration of molecules by creating a tortuous or circuitous path along which the drug or other active agent must migrate to avoid the intermittent barriers formed by the dispersed non-hydrophilic region 56. In this way, the dispersed non-hydrophilic region 56 creates an effective diffusion path that is greater than the actual thickness of the backing layer 52. In addition, the non-hydrophilic region 56 reduces the surface area through which water, drugs, or other active agents can diffuse through. In this way, the effective area for diffusion is smaller than the actual surface area of the backing layer 52.

Figure 6:
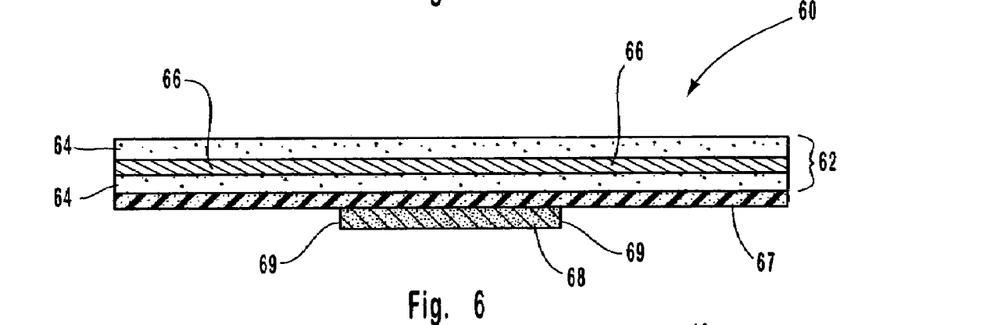
FIG. 6 is a cross-section view illustrating an alternative transmucosal delivery device according to the invention comprising a dissolvable backing layer that includes distinct hydrophilic and non-hydrophilic regions, an adhesive layer adjacent to the backing layer, and an active layer adjacent to and circumscribed by the adhesive layer.

FIG. 6 depicts an alternative transmucosal delivery device 60 according to the invention comprising a water-dissolvable backing layer 62 having a hydrophilic region 64 bifurcated into two layers or subregions by a non-hydrophilic layer 66. An adhesive layer 67 is disposed adjacent to an entire length of the backing layer 62. An active layer 68 is disposed adjacent to a portion of adhesive layer 67. The backing layer 62 and adhesive layer 67 extend beyond and circumscribe an outer perimeter 69 of the active layer 68. In this manner, the adhesive layer 67 forms an effective seal around the perimeter 69 of the active layer 68 when the delivery device 60 is attached to a mucosal surface (not shown).

Figure 7:
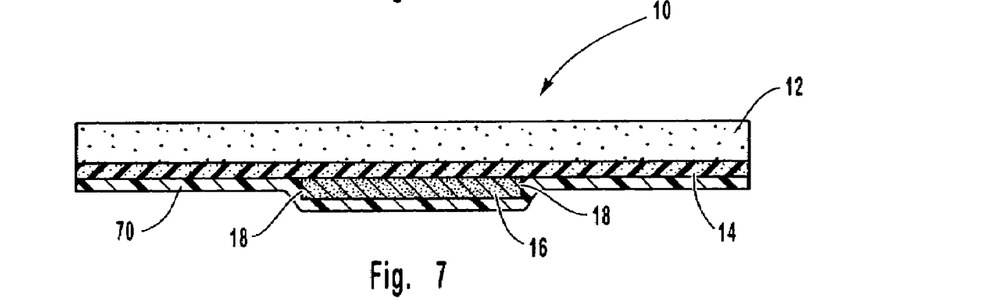
FIG. 7 depicts the transmucosal delivery device of FIG. 1 with a temporary protective layer covering the adhesive and active layers.

FIG. 7 depicts the delivery device of FIG. 1, but with a removable protective barrier 70 over exposed surfaces of the adhesive layer 14 and the active layer 16. The purpose of the removable barrier 70 is to protect the adhesive layer 14 and drug layer 16 from being contaminated. It can also serve to provide a nonstick surface until it is desired to attach the delivery device 10 to a mucosal surface (not shown). In use, the protective barrier 70 is removed and the exposed adhesive layer 14 of the delivery device 10 is placed against the mucosal surface.

Figure 8:
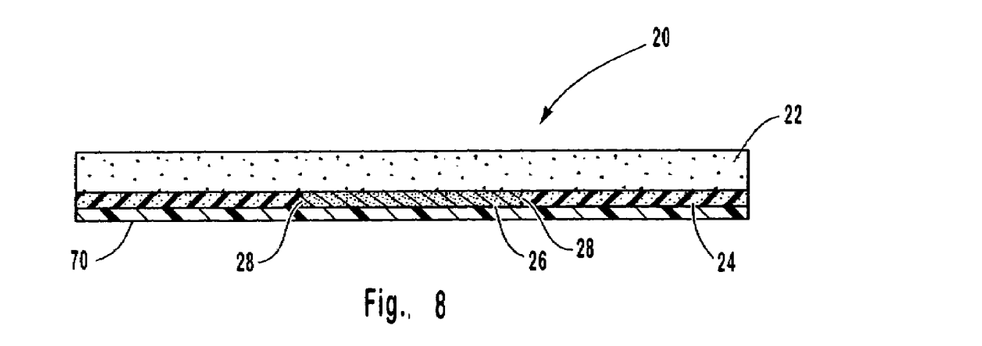
FIG. 8 depicts the transmucosal delivery device of FIG. 2 with a temporary protective layer covering the adhesive and active layers.

FIG. 8 similarly depicts the transmucosal delivery device of FIG. 2 with the protective barrier 70 attached to exposed surfaces of the adhesive layer 24 and the active layer 26.

The removable protective barrier or layer 70 may comprise any desired material, including either water soluble or non-water soluble plastics. In an alternative embodiment, a removable non-water soluble or water soluble barrier can be placed against an exposed surface of the backing layer of transmucosal delivery devices according to the invention.

EXAMPLES

The following examples are given by way of illustration and not limitation. Examples that are expressed in the past tense define actual compositions of drug delivery devices that have been manufactured. Examples that are expressed in the present tense are merely hypothetical or prophetic in nature but are based on, or extrapolated from, actual compositions that have been made.

Example 1

A transmucosal drug delivery device was manufactured having a dissolvable backing layer, an adhesive layer, and an active layer. The dissolvable backing layer was manufactured from 20% gelatin and 10% glycerin in water, which together formed a hydrophilic region, and gaseous voids dispersed throughout the hydrophilic region as a dispersed non-hydrophilic region. The hydrophilic region comprised 50% by volume of the backing layer while the voids comprised 50% by volume. The backing layer was cast on a plastic substrate. The thickness of the backing layer was 2 mm when cast.

The adhesive layer comprised 2.5% Polyox® 750 (a polyethylene oxide, water soluble resin), 0.5% Carbopol® 971 (a polyacrylic acid, water soluble material) in water. It was cast directly onto the solidified backing layer. The thickness of the adhesive layer was 1 mm when cast.

The active layer comprised 6% sodium alginate, 4% sumatriptan as a succinate salt, and 2% sodium taurocholic acid in water. The active layer was cast directly onto the exposed surface of the solidified adhesive layer.

Example 2

An oral transmucosal delivery patch containing an interferon as the active agent was made according to the current invention and used in a clinical test. The patch had three layers: (1) an active layer, (2) an adhesive layer, and (3) a backing layer. The formulations of the three layers are listed in the following tables.

| Active Layer Ingredients | |
| --- | --- |
| Ingredient Name | Concentration (%) |
| Sodium Alginate | 2% |
| Interferon α2b | 0.1% |
| Sodium Taurocholate | 0.8% |
| Water | 97.1% |

| Adhesive Layer Ingredients | |
| --- | --- |
| Ingredient Name | Concentration (%) |
| Polyethylene oxide | 2.5% |
| Polyacrylic acid | 0.5% |
| Water | 97.5% |

| Backing Layer Ingredients | |
| --- | --- |
| Ingredient Name | Concentration (%) |
| Gelatin | 20% |
| Glycerin | 10% |
| Dodecyltrimethylammonium Bromide | 0.1% |
| Water | 69.9% |

A gel composition used to form the active layer was prepared by mixing the sodium alginate, interferon α2b, and sodium taurocholate as dry ingredients in a mixing can. Then an appropriate amount of water was added. The mixing can was rolled slowly on a roller mixer to avoid trapping excessive air inside the gel. Once the gel was adequately mixed (i.e. the gel appears homogeneous with no visible lumps or particles), it was pipetted onto a plurality of 0.875 inch polystyrene disks at 1 ml per disk to form an active layer. The gel was dried at room temperature overnight.

A gel composition used to form the backing layer was prepared by mixing the gelatin, glycerin and dodecyltrimethylammonium bromide in 55° C. water. Once the gelatin was fully dissolved, an overhead mixer was used to whip the gel at 1500 rpm until the gel turned white and the volume doubled so as to form a foamed gel composition. The foamed gel composition was then cast in a plastic mold having a diameter of 1 inch and a thickness of 0.125 inch. The cast gel composition was allowed to dry at room temperature overnight to form a backing layer comprising approximately 50% by volume void spaces.

A gel composition used to form the adhesive layer was prepared by roll-mixing the ingredients in a mixing can. A thin layer, about 1 mm in thickness, was applied to the exposed surface of the dried backing layer. The combined backing and adhesive layers were dried together overnight at room temperature.

Once the backing, adhesive and active layers were ready, 25 μl of water was pipetted onto an exposed surface of the adhesive layer, and the active layer was peeled from the polystyrene disk and placed onto the moistened adhesive layer surface. The active layer was pressed gently until it sat flat on top of the adhesive/backing layer. The combined patch was then allowed to dry at room temperature.

In an in vivo study, an anesthetized dog was placed on the table with its mouth held open. The dog's cheek was laid on a flat surface so that the buccal tissue was flat and exposed. The buccal tissue was washed several times with saline and dried with a piece of gauze. Before placing the patch against the dog's buccal tissue, 200 μl of a saline solution was pipetted on the surface to mimic a normal wet oral mucosal surface. Once the patch was attached to the buccal tissue, two pieces of 1"×1.5" Telfa® pad (surgical dressing, Kendall Co.) soaked with 2.5 ml saline was placed on top of the patch to simulate the wet environment of the oral cavity. The Telfa® pads were replaced every 10 minutes to mimic normal conditions within the oral cavity (i.e., wear and tear). The patch was completely dissolved after about 60 minutes.

Figure 9:
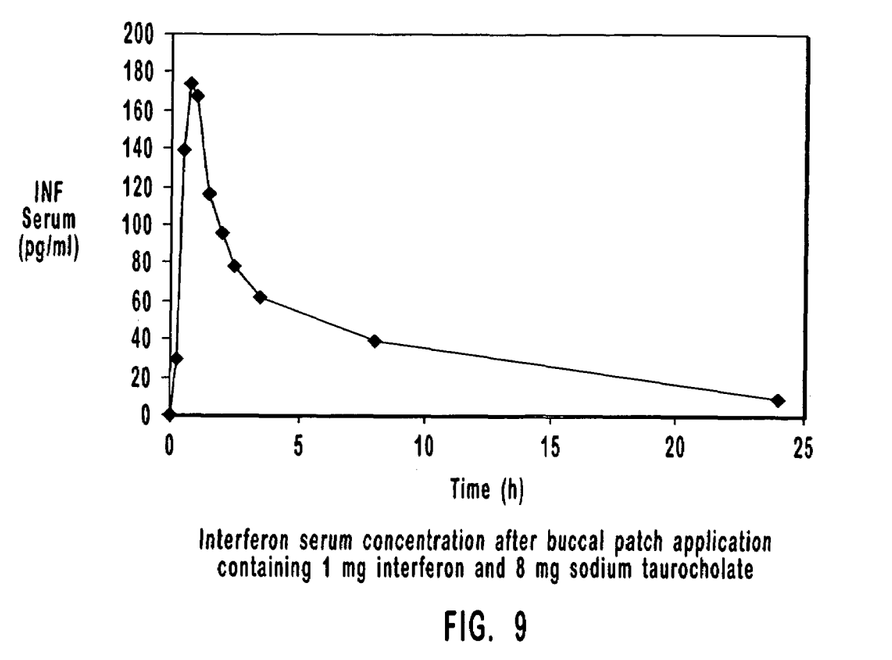
FIG. 9 depicts a graph that shows the blood serum concentration of interferon at various time intervals during an in vivo study.

Serum samples from the dog were taken at the following hourly intervals: 0, 0.25, 0.5, 0.75, 1, 1.5, 2, 2.5, 3.5, 8, and 24 hours. The graph depicted in FIG. 9 shows the serum interferon α2b concentration at the tested intervals during the 24 hour period. The serum concentration reached its peak ($C_{Max}$) at 1 hour ($t_{Max}$). The data showed that the backing provided enough protection so that the drug can be delivered across the oral mucosa. Once the backing dissolved, the drug delivery was stopped and the drug concentration started to decline immediately.

Example 3

An oral transmucosal delivery patch containing sumatriptan as the active agent was made according to the current invention and used in a clinical test. The patch had three layers: (1) an active layer, (2) an adhesive layer, and (3) a backing layer. The formulations of the three layers are listed in the following tables.

| Active Layer Ingredients | |
| --- | --- |
| Ingredient Name | Concentration (%) |
| Sodium Alginate | 4% |
| Sumatriptan Succinate | 11.2% |
| Sodium Taurocholate | 4% |
| Water | 80.8% |

| Adhesive Layer Ingredients | |
| --- | --- |
| Ingredient Name | Concentration (%) |
| Polyethylene oxide | 2.5% |
| Polyacrylic acid | 0.5% |
| Water | 97.5% |

| Backing Layer Ingredients | |
| --- | --- |
| Ingredient Name | Concentration (%) |
| Gelatin | 20% |
| Glycerin | 10% |
| Sodium Alginate | 0.25% |
| Acesulfame Potassium | 0.075% |
| Water | 69.675% |

A gel composition used to form the backing layer was made by dissolving the gelatin in 50° C. water containing the glycerin and sodium alginate. The gel was put in an oven heated to 50° C. to cause the gelatin to dissolve completely. Once the gelatin was thoroughly dissolved, the acesulfame potassium was added as sweetener. The gel composition was aerated by a high shear homogenizer to yield a foamed gel composition. The gel composition was cast on a plastic release liner to form an unsolidified sheet having a thickness of 2.2 mm using a casting block. The sheet was allowed to solidify without drying.

A gel composition used to form the adhesive layer was made by dissolving the non-water ingredients in the water. The adhesive gel composition was mixed under vacuum for about 6 hours until the gel became clear without lumps. The adhesive gel composition was cast on the solidified, but not dried, backing layer formed in the immediately preceding paragraph. The setting for the casting block was maintained at 2.2 mm. Since the backing layer shrank to about 1.2 mm upon solidifying, the actual thickness of the adhesive layer was about 1 mm. The combined backing/adhesive layers were allowed to dry at room temperature overnight.

A gel composition used to form the active layer was made by dry mixing the non-water ingredients in a mixing container and then roll-mixing the gel on a roller for 6 hours after addition of the water. The active gel composition was sonicated for a few minutes to eliminate air bubbles. A plastic mold having a plurality of mold cavities with a diameter of 0.6875 inch and a thickness of 0.5 mm was placed over a portion of the backing/adhesive layer. The active gel composition was cast inside the plastic mold cavities and the excess gel composition was cut using a stainless steel blade. The plastic mold was then removed. Once the active layer was dried, tri-layer patches were cut out using a 0.8125 inch diameter die cutter. The finished products were tri-layer patches in which the active layers were smaller than (i.e., circumscribed by) the backing/adhesive layers.

Figure 10:
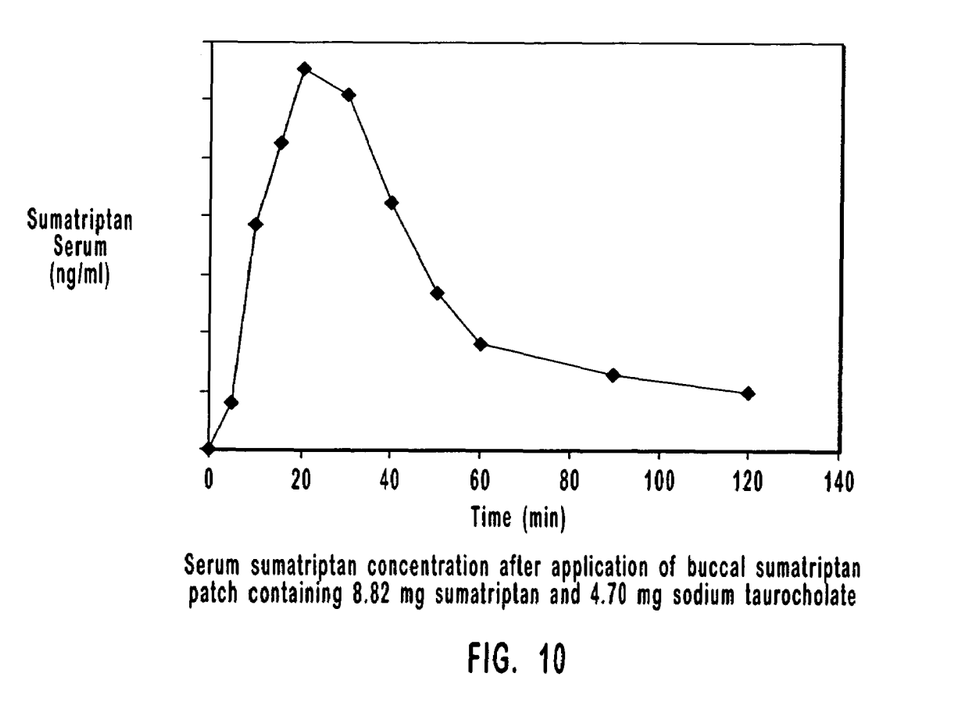
FIG. 10 depicts a graph that shows the blood serum concentration of sumatriptan at various time intervals during an in vivo study.

The graph depicted in FIG. 10 shows the results of an in vivo animal study using the tri-layer oral transmucosal sumatriptan patch. The animal study setting was similar to Example 2. The only difference was that the initial amount of saline was 100 μl and the interval of changing the Telfa® pad (surgical dressing, Kendall Co.) was 5 minutes. The idea was to simulate a more vigorous oral environment for the patches. In the animal study, the backing layer started to dissolve after about 15 minutes. Most of the backing layer had dissolved after about 30 minutes. The blood serum concentrations for sumatriptan corresponded well with the visual observation, i.e., the backing layer offered about 20 minutes of protection of the active formulation. Once the backing dissolved, the protection was gone, and the drug concentration started to decline rapidly.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A transmucosal delivery device for delivering a drug or other active agent through a mucosal membrane while confining the drug or other active agent within a defined area during delivery, the delivery device comprising:
   an active layer comprising at least one drug or other active agent and having an outer perimeter;
   a water-dissolvable backing layer comprising at least one hydrophilic polymer, said backing layer extending over said active layer and beyond said outer perimeter of said active layer in order for an overlapping portion of the backing layer to circumscribe said active layer; and
   an adhesive layer adjacent to said backing layer comprising at least one mucoadhesive adapted to adhere to a mucosal surface, at least a portion of said adhesive layer extending beyond said outer perimeter of said active layer and being adapted to seal said overlapping portion of said backing layer against the mucosal surface;
   the backing layer being adapted to protect said adhesive layer from over-moistening when the transmucosal delivery device is placed against the mucosal surface so as to maintain a seal against the mucosal surface and confine the drug or other active agent within a defined area against the mucosal surface.

2. A transmucosal delivery device as defined in claim 1, wherein said active layer comprises at least one component selected from the group consisting of fentanyl, morphine, other opiates, sumatriptan, other triptans, heparin, interferon, protein, and peptide.

3. A transmucosal delivery device as defined in claim 1, wherein said active layer comprises at least one enhancer that increases the rate at which said drug or other active agent penetrates the mucosal surface.

4. A transmucosal delivery device as defined in claim 1, wherein said active layer comprises at least one matrix material.

5. A transmucosal delivery device as defined in claim 4, wherein said matrix material comprises at least one member selected from the group consisting of alginic acid, alginic acid salt, cellulose, cellulose ether, cellulose ether salt, starch, carrageenan, polyethylene glycol, polyethylene oxide, polyvinyl alcohol, polyvinyl pyrrolidone, acacia, polyacrylic acid polymer, polyacrylic acid copolymer, and derivatives thereof.

6. A transmucosal delivery device as defined in claim 1, wherein said hydrophilic polymer comprises at least one hydrogel.

7. A transmucosal delivery device as defined in claim 6, wherein said hydrogel comprises at least one component selected from the group consisting of gelatin, caseine, other protein-based material, pectin, agar, chitosan, carrageenan, starch, modified starch, dextran, methylcellulose, calcium carboxymethylcellulose, sodium carboxymethylcellulose, a cross-linked polymer of sodium carboxymethylcellulose, microcrystalline cellulose, ethylcellulose, hydroxyethylcellulose, hydroxypropylcellulose, hydroxypropylmethylcellulose, hydroxylpropylmethylcellulose phthalate, other cellulosic ether, cellulose acetate, cellulose acetate phthalate, other cellulose derivative, polyvinyl alcohol, polyvinylpyrrolidone, cross-linked povidone, other vinyl polymer, other vinyl copolymer, guar gum, poloxamer, polyethylene glycol, polyethylene oxide, a polyacrylic acid, a polyether, an alkoxy polymer, sodium alginate, xanthan gum, other natural hydrogel, a hydrogel derived from natural products, and derivatives thereof.

8. A transmucosal delivery device as defined in claim 1, wherein said backing layer further comprises at least one plasticizer.

9. A transmucosal delivery device as defined in claim 8, wherein said plasticizer comprises at least one component selected from the group consisting of glycerol, propylene glycol, polyethylene glycol, polypropylene glycol, sugar alcohol, and corn syrup.

10. A transmucosal delivery device as defined in claim 1, wherein said hydrophilic polymer is adapted to dissolve over time when exposed to moisture.

11. A transmucosal delivery device as defined in claim 1, wherein said backing layer comprises a formulation and thickness wherein the backing layer dissolves when exposed to moisture within a prescribed time period or range of time periods.

12. A transmucosal delivery device as defined in claim 1, wherein said backing layer comprises a formulation and thickness wherein said backing layer dissolves when exposed to moisture within a time period in a range from about 5 minutes to about 2 hours.

13. A transmucosal delivery device as defined in claim 1, wherein said backing layer inhibits migration of water, a drug or other active agent through said backing layer, to or from the active layer, within a prescribed time period.

14. A transmucosal delivery device as defined in claim 1, wherein said backing layer comprises a sheet or film having a thickness in a range of about 0.1 microns to about 5 millimeters.

15. A transmucosal delivery device as defined in claim 1, wherein said adhesive layer comprises at least one component selected from the group consisting of polyacrylic acid polymer, polyethylene oxide, polyacrylic acid copolymer, polyethylene glycol, starch, cellulosic ether, cellulose ether salt, carrageenan, sodium alginate, and derivatives thereof.

16. A transmucosal delivery device as defined in claim 1, wherein said adhesive layer extends from the outer perimeter of said active layer to an outer perimeter of said backing layer.

17. A transmucosal delivery device as defined in claim 1, wherein a portion of said adhesive layer is disposed between said backing layer and said active layer.

18. A transmucosal delivery device as defined in claim 1, wherein the delivery device is a buccal patch.

19. A transmucosal delivery device as defined in claim 1, wherein said water-dissolvable backing layer comprises:
  a hydrophilic region comprising at least one hydrophilic polymer and that is adapted to dissolve over a prescribed period of time when exposed to moisture; and
  at least one non-hydrophilic region, at least partially or wholly encapsulated within said hydrophilic region, that is adapted to inhibit migration of water, the drug or other active agent through said backing layer and that is adapted to disperse when no longer encapsulated within said hydrophilic region.

20. A transmucosal delivery device as defined in claim 19, wherein said hydrophilic region comprises a continuous phase and said non-hydrophilic region comprises a disperse phase.

21. A transmucosal delivery device as defined in claim 19, wherein said hydrophilic region comprises a continuous phase and said non-hydrophilic region comprises a continuous phase.

22. A transmucosal delivery device as defined in claim 19, wherein said non-hydrophilic region comprises at least one component selected from the group consisting of gaseous voids, hydrophobic liquid droplets, hydrophobic solid particles, non-dissolvable solid particles, oils, fats, fatty acids, salts of fatty acids, waxes, organic polymers, silicone, and inorganic filler particles.

23. A transmucosal delivery device as defined in claim 19, wherein said non-hydrophilic region comprises at least one solid component that transforms into a liquid or softened solid when warmed to body temperature.

24. An oral transmucosal delivery device for delivering a drug or other active agent, in contact with a mucosal membrane, through the mucosal membrane while inhibiting migration of water through a backing layer into the layer containing the drug or other active agent, and while inhibiting migration of the drug or other active agent through the backing layer into the oral cavity, the delivery device comprising:
  an active layer comprising a drug or other active agent and having an outer perimeter;
  a water-dissolvable backing layer comprising gelatin and gaseous voids dispersed therein, the backing layer extending over the active layer and beyond the outer perimeter of the active layer in order for an overlapping portion of the backing layer to circumscribe the active layer; and
  an adhesive layer adjacent to the backing layer comprising at least one polyacrylic acid polymer or polyacrylic acid copolymer adapted to adhere to a mucosal surface in an oral cavity, at least a portion of the adhesive layer extending beyond the outer perimeter of the active layer and being adapted to seal the overlapping portion of the backing layer against the mucosal surface;
  the backing layer being adapted to protect the adhesive layer from saliva when the transmucosal delivery device is placed against mucosa in an oral cavity so as to maintain a seal against the mucosa;
  the backing layer being adapted to inhibit migration of water through the backing layer into the active layer; and
  the backing layer being adapted to inhibit migration of the drug or other active agent through the backing layer into the oral cavity.

25. An oral transmucosal delivery device for delivering a drug or other active agent, in contact with a mucosal membrane, through a mucosal membrane while confining the drug or other active agent within a defined area during delivery, the delivery device comprising:
  an active layer comprising at least one drug or other active agent and having an outer perimeter;
  a water-dissolvable backing layer extending over the active layer and beyond the outer perimeter of the active layer in order for an overlapping portion of the backing layer to circumscribe the active layer, wherein the backing layer comprises:

a hydrophilic region comprising at least one hydrophilic polymer and that is adapted to dissolve over a prescribed period of time when exposed to moisture; and at least one non-hydrophilic region, at least partially or wholly encapsulated within the hydrophilic region, that is adapted to inhibit migration of water, the drug, or other active agent through the backing layer and that is adapted to disperse when no longer encapsulated within the hydrophilic region; and an adhesive layer adjacent to the backing layer comprising at least one mucoadhesive polymer adapted to adhere to a mucosal surface in an oral cavity, at least a portion of the adhesive layer extending beyond said outer perimeter of the active layer and being adapted to seal the overlapping portion of the backing layer against the mucosal surface, the backing layer being adapted to protect the adhesive layer from saliva when the transmucosal delivery device is placed against the mucosa in an oral cavity so as to maintain a seal against the mucosa and confine the drug or other active agent within a defined area against the mucosa.

* * * * *